United States Patent [19]
Perlman

[11] Patent Number: 5,230,832
[45] Date of Patent: Jul. 27, 1993

[54] GALACTOMANNAN-AGAROSE BINARY GEL FOR NUCLEIC ACID ELECTROPHORESIS

[75] Inventor: Daniel Perlman, Arlington, Mass.

[73] Assignee: Brandeis University, Waltham, Mass.

[21] Appl. No.: 645,203

[22] Filed: Jan. 24, 1991

[51] Int. Cl.$^5$ .................. B01J 13/00; C25B 7/00; B01D 61/42; G01N 27/26

[52] U.S. Cl. .................. 252/315.3; 252/315.4; 204/182.8; 204/299 R; 522/911; 521/50.5

[58] Field of Search .................. 252/315.3, 315.4; 522/88, 910, 911; 536/114; 436/515; 521/50.5; 204/182.8, 182.7, 182.9, 299 R; 427/36; 264/22

[56] References Cited

U.S. PATENT DOCUMENTS

| | | | |
|---|---|---|---|
| 3,034,974 | 5/1962 | Lowry | 536/114 X |
| 4,290,911 | 9/1981 | Cook et al. | 252/316 |
| 4,321,121 | 3/1982 | Gurske | 204/180 |
| 4,704,198 | 11/1987 | Ebersole et al. | 204/182.8 |
| 5,114,550 | 5/1992 | Schomberg et al. | 204/180.1 X |

OTHER PUBLICATIONS

Chemical Abstracts, CA 70(15): 65022y.
Perlman et al., Analytical Biochemistry, 163, 247–254 (1987).
Peacock et al., Biochemistry, 7(2), 668–674 (1968).

*Primary Examiner*—Robert L. Stoll
*Assistant Examiner*—Daniel S. Metzmaier
*Attorney, Agent, or Firm*—Lyon & Lyon

[57] ABSTRACT

A method for forming an agarose electrophoretic gel by addition of gamma-irradiated clarified galactomannan ($\gamma$CGM) to optically clarify the gel and improve the electrophoretic fractionation and resolution of oligonucleotides differing in molecular weight. The gel includes agarose, an electrophoretic buffer for nucleic acids, and a CGM vegetable gum subjected to between 0.1 and 4.0 megarads of ionizing gamma radiation.

9 Claims, No Drawings

GALACTOMANNAN-AGAROSE BINARY GEL FOR NUCLEIC ACID ELECTROPHORESIS

BACKGROUND OF THE INVENTION

This invention relates to agarose and galactomannan-containing electrophoretic gels. Agarose is a polysaccaride purified from agar-agar and commonly used to form aqueous buffered electrophoretic gels for nucleic acid fractionation. Various other hydrocolloid polymers of synthetic or natural origin including polyacrylamide and galactomannan have been combined with agarose for the electrophoresis of nucleic acids and other macromolecules. For example Peacock et al., *Biochemistry*, 7, No. 2, 668–674 (1968) utilize acrylamide gels strengthened with agarose for separation and analysis of RNAs. Cook et al., U.S. Pat. No. 4,290,911 utilize an agarose gel containing a clarified galactomannan gum (CGM), such as clarified locust bean gum (CLBG) for isoelectric focussing in which differences in net charge among protein molecules are used to separate the molecules in the gel. Gurske, U.S. Pat. No. 4,321,121 combines an acid polysaccharide or a galactomannan polysaccharide with a gelling polysaccharide such as agarose to form an electrophoretic gel. The gel compositions of Gurske are said to improve the separation of protein isoenzymes having differences in electrical charge but similar molecular weights.

Perlman et al. in *Analytical Biochemistry*, 163, 247–254 (1987) describe use of locust bean gum galactomannan in combination with agarose and Tris-borate-EDTA (TBE) buffer to fractionate DNA fragments.

SUMMARY OF THE INVENTION

In the present invention, methods have been found to form useful composite agarose-CGM-containing electrophoretic gels for nucleic acid fractionation. By use of specific buffer compositions and gamma-irradiated CGM or CLBG ($\gamma$CGM or $\gamma$CLBG), the gelling process is slowed, and the viscous and rubbery nature of CLBG-agarose mixed solutions is reduced. This allows higher concentrations of $\gamma$CLBG, compared to the conventional CLBG previously used, to be employed in casting clear bubble-free electrophoretic gels. These higher concentrations of $\gamma$CLBG improve separation and resolution of DNA molecules differing in size. The gels described herein have recently been found to possess an enhanced and useful clarity both before and after ethidium bromide staining. This surprising gel clarification, arising from an alteration of the optical properties of gelled agarose, is induced by $\gamma$CLBG addition and is superior to that of simple agarose gels having the same agarose concentration but which lack $\gamma$CLBG.

In general, the present invention features a method for making an agarose electrophoretic gel using $\gamma$CGM to obtain a gel which exhibits superior transparency, greater nucleic acid loading capacity, improved resolution of nucleic acid fragments as a function of molecular weight, and greater resistance to tearing and puncture than comparable prior art agarose electrophoretic gels. The composite gel is formed from agarose and a $\gamma$CGM vegetable gum, such as commercial CLBG which has been gamma-irradiated to radiolytically alter its structure and reduce the viscosity of a resulting aqueous buffered solution of the $\gamma$CGM to a predetermined level. Clarified guar, tara or cassia gum (filter-clarified in the laboratory) can also be utilized as alternative galactomannan sources. Each of these gums remains stable as a clear solution at room temperature (20°–25° C.).

Gamma radiation treatment of the CGM involves exposing the CGM to ionizing radiation which chemically alters its structure and reduces its viscosity to a desired useful range.

In the present invention, $\gamma$CLBG is prepared and utilized in the electrophoresis of nucleic acids for the first time. Applicant has also discovered that certain electrophoretic buffer compositions including phosphate and acetate-buffered Tris-EDTA solutions, when combined with $\gamma$CLBG and agarose, produce a non-rubbery gel (as compared to the rubbery gels of Perlman et al. supra). This non-rubbery consistency reduces the tendency of these agarose sol compositions to trap air bubbles which would complicate formation of homogeneous electrophoretic gels which must be bubble-free. In the present invention, the gamma irradiation of CGM coupled with the use of appropriate electrophoretic buffers, allows the combination of a wide range of $\gamma$CGM concentrations with agarose to produce sols having moderate viscosities which are, in turn, easily cast to form gels. The feasibility of using $\gamma$CGM concentrations up to 5% (w/v) in agarose gels without trapping air bubbles has, in turn, been found to allow improved fractionation of small nucleic acid fragments (10–2000 base pairs) based upon molecular weight differences among these fragments.

Surprisingly, $\gamma$CGM addition to agarose gels has been found to induce clarification of gelled agarose and actually reduces the spectrophotometrically measured optical turbidity (optical density) of the agarose gel. The reason why the $\gamma$CGM additive reduces the amount of haze in the composite electrophoretic gel is unknown but may be caused by an alteration in the gelled agarose structure. This feature is advantageous since gel clarity is particularly important for photography after staining with a dye such as UV-fluorescent ethidium bromide.

In a first aspect, the invention features a method for modifying an agarose gel by addition of $\gamma$CGM for the purpose of optically clarifying the gel by reducing the intrinsic haze of gelled agarose while improving the electrophoretic fractionation and resolution of nucleic acids, i.e., oligonucleotides, differing in molecular weight. The modified gel has a reduced haze compared to an agarose gel containing the same concentration of agarose but lacking said gamma-irradiated galactomannan. The method of agarose gel modification includes several steps including first subjecting CGM in dry solid form to between 0.1 and 4.0 megarads of ionizing gamma radiation to produce $\gamma$CGM. This radiation treatment results in the $\gamma$CGM vegetable gum having an absolute viscosity of between 10 and 1000 centipoise (cp) for a 1% weight per unit volume (w/v) solution of the $\gamma$CGM in distilled water at 25° C. Secondly, approximately 0.1%–5.0% (w/v) of this $\gamma$CGM is combined with approximately 0.2–2.0% (w/v) agarose (electrophoretic grade) in an aqueous electrophoretic buffer. This buffer, which typically contains the phosphate or acetate anion, maintains constant pH and chemical stability of the nucleic acids during electrophoresis. The mixture of $\gamma$CGM, agarose and electrophoresis buffer is then heated to approximately 100° C. to form a clear sol, and finally cast and cooled to form a clarified electrophoretic gel.

In preferred embodiments, the invention features the use of an agarose which has an electroendosmosis value ($-M_r$) greater than or approximately equal to 0.10 whereby the agarose can chemically interact with the galactomannan to produce a gel of increased mechanical strength compared to a similar gel lacking this galactomannan. In another preferred embodiment the invention is used to resolve oligonucleolides containing less than 2000 nucleotides and may be used to fractionate and resolve two oligonucleotides each containing no more than 200 nucleotides and differing from one another by no more than 10 nucleotides.

In other preferred embodiments, a concentration of approximately 0.5% (w/v) γCGM reduces the optical haze in a 2% (w/v) agarose-containing gel, as measured by optical density at a wavelength of 650 nm, by at least 25%. Thus, by introducing γCGM into agarose electrophoretic gels, the method of the present invention permits improved photodocumentation of gels, e.g., ethidium bromide-stained nucleic acid-containing gels.

In yet other preferred embodiments, the gel composition utilized in the method of the present invention preferably employs a mixture containing 0.4%–1.0% (w/v) agarose and 0.2%–4% (w/v) γCGM prepared by subjecting commercial CGM in dry powdered form to between 0.1 and 4.0 megarads of ionizing gamma radiation to produce a radiolytically altered CGM having a viscosity between 20 and 500 cp for a 1% (w/v) solution in distilled water at 25° C.

In an especially preferred embodiment, the invention features the use of an electrophoretic buffer selected from the group consisting of phosphate, acetate and Tris (hydroxymethyl) aminomethane buffers such as phosphate and acetate-buffered Tris-EDTA solutions at a pH of approximately 8.0 to control the rate of gellation, rheology and viscosity of the gel-forming mixture.

The phosphate buffer is formed by dissolving in distilled water at the following final concentrations, 0.04M Tris (hydroxymethyl) aminomethane (Tris base), 0.004M disodium ethylenediamine tetraacetate (EDTA), and adding sufficient phosphoric acid to bring the final solution pH to 8.0. The acetate buffer is formed by dissolving in distilled water at the following final concentrations 0.04M Tris base, 0.002M EDTA, and adding sufficient glacial acetic acid to bring the final solution pH to 8.0. A preferred source of CGM utilized as the starting material for producing γCGM in this invention is CLBG.

Other features and advantages of the invention will be apparent from the following description of the preferred embodiments thereof, and from the claims.

DESCRIPTION OF THE PREFERRED EMBODIMENTS

Clarified Galactomannan

The term "clarified galactomannan" has been previously defined in the patent literature by Cook et al., U.S. Pat. No. 4,290,911. In the context of the present invention, CGM means a purified galactomannan vegetable gum free from hull fragments and soluble by itself in water without gelling, at temperatures up to and including 100° C., to form an essentially clear solution. For example, one commercially available clarified CGM useful as a starting material for producing the final material useful in the present invention is CLBG purified from locust bean gum and is obtained from the FMC Corporation (Gelloid LB 230). It dissolves in hot water, with a 1% (w/v) solution having a viscosity of about 2500 cps at 25° C. This material, preferably in the dry solid form, must be treated by gamma irradiation to produce γCLBG for use in the present invention. Vegetable gum galactomannans useful as starting materials for the present invention are those polysaccharides that include a (1→4)-β-D-mannan main chain polymer to which are attached single α-D-galactopyranosyl groups at the 0-6 position of some of the D-mannopyranosyl residues. The most readily available commercially clarified CGM is purified from locust bean gum which is extracted from locust bean kernel endosperms of the tree pods of *Ceratonia siliqua*. Commercial galactomannan such as cassia gum and locust bean gum (commonly used in textile and paper manufacture) is unclarified and, as such, is unsuitable for use in the present invention because it contains hull fragments and/or other impurities. These impurities produce cloudy solutions alone, or in combination with dissolved agarose, and must be carefully removed by centrifugation and/or solution filtration or by other means to generate clarified products useful in the present invention.

In preferred embodiments of the above aspects, the CGM starting material is selected from the group consisting of CLBG, tara gum, guar gum and cassia gum; most preferably the CGM is CLBG. The viscosity of commercially available CLBG, as for example Gelloid LB 230 described above is approximately 2500 cp for a 1% (w/v) solution in distilled water at 25° C. During radiolytic modification of the CLBG by ionizing gamma radiation the viscosity is reduced to between 10 and 1000 cp and preferably 20–500 cp for a 1% (w/v) solution in distilled water at 25° C. Radiolytic modification is preferably accomplished by either cobalt-60 or Cs-137 gamma irradiation (or its equivalent) of commercial dry solid CGM, e.g., CLBG powder at room temperature using between 0.1 and 4.0 megarads of radiation. Generally 0.25–2.0 megarads of gamma irradiation is effective in producing the desired degree of modification of the CGM and reducing the viscosity to a range between 250 and 25 cp for a 1% (w/v) solution in distilled water at 25° C. Co-60 irradiation exposes the CGM to gamma rays having energies of 1.17 and 1.33 mev while Cs-137 irradiation provides exposure to 0.66 mev gamma rays. Exposure to radiation from either isotope is effective for the purposes of the present invention. The irradiation treatment when employed at a level of approximately 1.0 megarad or greater has the added benefit of leaving the dry solid CGM, e.g., CLBG, essentially sterile. With sterile CGM powder, a sterile electrophoretic gel composition can be conveniently formulated by dissolving the CGM in sterile buffer. This aqueous gel composition can subsequently be stored for a long period of time without degradation due to mold or bacterial growth.

The present invention provides an electrophoretic gel which has many of the desirable properties of agarose gels but lacks most of the haze normally present in such gels (see Example 1). This haze interferes with the visual analysis and photodocumentation of such gels. For example, reducing agarose haze with the present invention makes it possible to photograph ethidium bromide-stained nucleic acid-containing gels and to detect DNA bands containing approximately one nanogram or less of DNA. Moreover, the resolution or separation and fractionation of oligonucleotides containing less than 2000 nucleotides is significantly improved in γCGM-containing gels compared to gels containing only agarose as evidenced by fractionating DNA fragments obtained from Msp I restriction enzyme cleavage of pBR322 DNA and BstE II cleavage of phage lambda DNA. Evidence for this stated improvement was obtained by casting side-by-side electrophoretic gels, containing either 2% (w/v) agarose (SeaKem LE electrophoresis grade agarose from FMC Corporation), 4% NuSieve agarose (also FMC Corporation), or 0.5% agarose (SeaKem LE agarose) supplemented with 2% (w/v) γCLBG (1.0 megarad gamma irradiated Gelloid LB 230 having a viscosity of approximately 40 cp at 25° C. for a 1% (w/v) solution in distilled water). All gels were cast using Tris-phosphate-EDTA buffer (0.04M Tris base, 0.004MEDTA, pH adjusted to 8.0 with phosphoric acid). The gels were loaded with the above-described DNA fragments and horizontally electrophoresed at 7 volts per centimeter. The gels were stained with ethidium bromide (0.5 μg/ml) for evaluating fractionation of the DNA. Besides improving the separation of DNA fragments containing less than 2000 nucleotides, the γCLBG-containing gel revealed significantly improved separation of pairs of DNA fragments each containing no more than 200 nucleotides and differing in size by no more than 10 nucleotides. Such fragments were easily detected in the electrophoretic separation of Msp I-digested pBR322 DNA.

The improved optical clarity of a 2% (w/v) γCLBG-containing agarose gel compared to a normal agarose-containing gel is evident under both visible and ultraviolet light. As is shown in Example 1, an increasing concentration of γCLBG added to a constant concentration of agarose results in a decreasing optical density (haze). The technical explanation for this clarifying effect has not yet been established but it is a valuable element of the present invention. The clarity of γCLBG-containing gels is particularly apparent in the ability to photograph and easily detect and resolve nanogram and subnanogram quantities of the ethidium bromide-stained 26 and 34 base pair DNA fragments in the electrophoresed Msp I digest of pBR322 DNA. Addition of as little as 0.10% (w/v) γCLBG to a 2.0% (w/v) agarose gel reduces haze in the binary gel as measured at the 650 nm wavelength by approximately 13% while the addition of 0.50% (w/v) of the gum reduces haze by about 30%.

In addition to clarifying agarose electrophoretic gels, the addition of γCGM according to the present invention also provides increased strength and elasticity in agarose gels. Gel strength is determined by measuring the force per unit area on a piston required to cause gel failure. Addition of only 0.1 to 0.3% (w/v) γCLBG to a 1.0% (w/v) agarose gel provides a significantly stronger gel (having strength comparable to a 2.0% (w/v) agarose gel lacking the galactomannan). For example, increases in gel strength achieved by addition of these γCGM concentrations range from approximately 250 to 500 g/cm$^2$.

A substantial cost-savings is also achieved by the supplementation and partial substitution of γCGM for agarose in a binary gel, given that the cost to produce the γCGM ingredient (such as γCLBG) is presently less than 10% the price of electrophoretic grade agarose.

The agarose used in this invention should possess a $-M_r$ value of approximately 0.10 or greater. Such agarose provides a gel with increased mechanical strength compared to agarose gels formed using agarose having a $-M_r$ value $<0.1$.

Additional characteristics of the γCLBG-agarose binary gels of the present invention which provide advantages over simple agarose gels for nucleic acid fractionation may be summarized as follows:

(i) γCLBG-agarose binary gels provide a more efficient structural network for the separation of nucleic acids based on their size. For example, a 0.5% (w/v) agarose gel containing only 1% (w/v) γCLBG retards the electrophoretic migration of 50 base-pair DNA fragments to a greater extent than a gel containing 2.5% (w/v) agarose. Simultaneously, the γCLBG-containing gel as a "vehicle" can carry a greater quantity of DNA than the agarose gel without DNA band tailing and smearing. Comparing the ability to electrophoretically carry Msp I-cleaved pBR322DNA, a 2% (w/v) γCLBG-containing gel can hold approximately twice as much DNA as a 4% (w/v) NuSieve agarose-containing gel without overloading. Surprisingly, the γCLBG gel is just as effective in fractionating small DNA fragments (~200 nucleotides or less) as the 4% (w/v) NuSieve agarose gel.

(ii) γCLBG-agarose binary gels exhibit "tighter", i.e., narrower electrophoretic banding of small oligonucleotides (particularly small DNA fragments containing 25-2000 base pairs) than comparable agarose gels. Applicant believes that the γCLBG which hydrogen bonds to the gelled agarose (and contributes significantly to the viscosity of the aqueous phase in the gel) reduces the rate of random diffusion of DNA in the gel's aqueous phase. Such diffusion is probably responsible for band broadening during the course of oligonucleotide electrophoresis in agarose gels.

The above-described advantages of γCLBG-containing agarose gels are in addition to those described earlier including improved transparency, mechanical strength, and reduced cost of materials.

EXAMPLE 1

Improved electrophoretic gel transparency is achieved by addition of γCLBG to agarose. A series of agarose electrophoretic gels was prepared containing increasing concentrations of 1.0 megarad gamma-irradiated CLBG (original starting material CLBG obtained from FMC Corporation-Gelloid LB 230). The optical density (OD) of these gels was monitored at 650 nm and 475 nm to measure gel turbidity. Such measurements reflect the amount of haze in a formed gel. Samples of agarose powder (0.100 g SeaKem LE agarose, FMC Corporation) were combined with increasing amounts of γCLBG powder and dissolved in 5.0 ml volumes of Tris-phosphate-EDTA electrophoresis buffer (Maniatis et al., Molecular Cloning-A Laboratory Manual) by autoclaving at 121° C. for 15 minutes. The resulting 2% (w/v) agarose solutions containing γCGM were solidified in disposable polystryene optical cuvettes for spectrophotometric measurements.

Gel compositions and optical densities are shown in Table 1. Percentage decreases in OD are calculated relative to the OD for the agarose gel lacking γCGM. These data show that γCGM addition enhances agarose gel transparency.

TABLE 1

| % (w/v) γCGM Added | OD 650 nm | % Decrease | OD 475 nm | % Decrease |
|---|---|---|---|---|
| 0.00 | .274 | — | .734 | — |
| 0.02 | .264 | 3.6 | .708 | 3.5 |
| 0.05 | .253 | 7.7 | .686 | 6.5 |

TABLE 1-continued

| % (w/v) γCGM Added | OD 650 nm | % Decrease | OD 475 nm | % Decrease |
| --- | --- | --- | --- | --- |
| 0.10 | .238 | 13.1 | .651 | 11.3 |
| 0.20 | .216 | 21.1 | .597 | 18.7 |
| 0.30 | .199 | 27.3 | .560 | 23.7 |
| 0.50 | .182 | 33.6 | .517 | 29.6 |

EXAMPLE 2

Formulating and casting of a γCGM-agarose electrophoretic gel according to the present invention is described herein. The agarose and γCGM polysaccharides may be combined with one another and with electrophoretic buffer either before or after dissolving the polysaccharides. For example, it is convenient to weigh out the agarose and γCGM powders and then moisten the mixed powder with ethanol to assure its dispersal (rather than clumping) upon addition of an appropriate volume of electrophoretic buffer. Acetate or phosphate-containing Tris-EDTA buffers are preferred over the commonly utilized borate-containing electrophoretic buffers which produce a highly viscous and rubbery agarose-galactomannan solution, complicating the process of gel casting. Examples of appropriate electrophoretic buffers include acetate and phosphate buffers containing 0.04M Tris base and 0.002M EDTA which have been titrated respectively with glacial acetic acid (to form Tris-acetate buffer) or phosphoric acid (to form Tris-phosphate buffer).

The steps used in forming a typical binary electrophoretic gel containing agarose and γCLBG are as follows for a 100 ml gel volume:

(i) 0.5 g of agarose powder (SeaKem LE agarose from FMC Corporation) is weighed out and placed in a dry flask;

(ii) approximately 1.0–2.0 g γCLBG (Gelloid LB 230 CLBG starting material from FMC) which, in dry solid (powdered) form, has been previously gamma-irradiated with Co-60 radiation to radiolytically alter its structure and reduce the viscosity of the CLBG to approximately 20–40 cp at 25° C., is weighed out and added to the above agarose powder;

(iii) a sufficient volume of ethanol is added to moisten the powder mixture;

(iv) approximately 98–99 ml Tris-phosphate buffer (above) is added to the mixture and the resulting suspension is heated to boiling (with swirling or stirring to prevent boil-over) and maintained above 90° C. until all of the particulate material has dissolved;

(v) the clear sol is cooled to approximately 60° C. and cast to form a gel. Prior to gel formation a comb is inserted into the sol to form sample loading wells;

(vi) after gel formation, the comb is removed and the gel is submerged in the same buffer (used to form the gel) within an electrophoresis chamber. Nucleic acid samples are then added to the sample wells and electrophoresis is commenced. An appropriate voltage gradient for these gels containing γCLBG and agarose is 5–10 volts per centimeter. A bromophenol blue tracking dye placed in the nucleic acid loading buffer in the above-described binary gel co-migrates with double-stranded DNA fragments containing approximately 40–60 nucleotides.

EXAMPLE 3

Controlled chemical alteration of commercial CGM and reduction of its viscosity by gamma irradiation. CLBG dry powder (Gelloid LB 230 obtained from the FMC Corporation) was gamma-irradiated by exposure to Co-60 radiation at 25° C. for increasing periods of time to generate exposure dosages ranging from 0.1 to 4.0 megarads. Subsequently, the kinematic viscosities for 1% (w/v) solutions of the irradiated CLBG samples were tested using a size 400 Cannon-Fenske viscometer (ASTM D2515 and D445 viscosity methods) which had been viscosity-calibrated with ethylene glycol. Absolute viscosities are presented below in Table 2 for several of the gamma dosages.

TABLE 2

| Dosage (megarads) | Viscosity (cp) at 25° C. |
| --- | --- |
| 0 | 2500 |
| 0.25 | 244 |
| 0.50 | 90 |
| 1.0 | 30 |
| 2.0 | 14 |

Other embodiments are within the following claims.

I claim:

1. A method for forming an agarose electrophoretic gel, comprising the steps of:
   subjecting clarified galactomannan (CGM) in dry solid form to between 0.1 and 4.0 megarads of ionizing gamma radiation to produce γCGM,
   combining in an aqueous electrophoretic buffer, 0.2%–2% (weight per volume of buffer, w/v) agarose, and 0.1%–5.0% (w/v) of said γCGM,
   heating said mixture of agarose, γCGM and buffer to form a clear sol; and
   casting and cooling said sol to form a clarified electrophoretic gel.

2. The method of claim 1 wherein said agarose has an electroendosmosis value $(-M_r)$ greater than, or equal to, 0.10.

3. The method of claim 1 wherein 0.5% (w/v) of said γCGM reduces the haze (measured by optical density at a wavelength of 650 nm) in a gel containing 2% (w/v) agarose by at least 25%.

4. The method of claim 1 wherein said mixture comprises 0.4%–1% (w/v) agarose and 0.2%–4% (w/v) γCGM which was subjected to between 0.25 and 2.0 megarads of ionizing gamma radiation.

5. The method of claim 1 wherein said electrophoretic buffer is selected from the group consisting of phosphate, acetate, and Tris (hydroxymethyl) aminomethane-buffered solutions.

6. The method of claim 1, 3 or 4 wherein said CGM is selected from the group consisting of clarified locust bean gum (CLBG), tara gum, guar gum, and cassia gum.

7. The method of claim 6 wherein said CGM is CLBG.

8. An agarose electrophoretic gel composition comprising 0.2%–2% (weight per volume of buffer, w/v) agarose, 0.1%–5.0% (w/v) gamma-irradiated CGM, and an aqueous electrophoretic buffer.

9. The composition of claim 8 wherein said buffer is selected from the group consisting of phosphate, acetate and Tris (hydroxymethyl)aminomethane.

* * * * *